United States Patent [19]

Simmonds

[11] Patent Number: 4,733,086

[45] Date of Patent: Mar. 22, 1988

[54] THERMAL ELECTRON SOURCE

[75] Inventor: Peter G. Simmonds, Dorset, England

[73] Assignee: The Secretary of State for Defence in Her Britannic Majesty's Government of the United Kingdom of Great Britain and Northern Ireland, London, England

[21] Appl. No.: 837,132

[22] Filed: Mar. 7, 1986

[30] Foreign Application Priority Data

Mar. 15, 1985 [GB] United Kingdom ............... 8506788

[51] Int. Cl.⁴ ............................................. H01J 27/20
[52] U.S. Cl. .................. 250/423 P; 250/427; 250/379; 250/382
[58] Field of Search ............... 250/423 R, 423 P, 424, 250/427, 379, 381, 382; 313/523, 541

[56] References Cited

U.S. PATENT DOCUMENTS

| 2,959,677 | 11/1960 | Robinson et al. | 250/382 |
| 3,277,296 | 10/1966 | Dimick et al. | 250/381 |
| 3,313,971 | 4/1967 | Negy | 250/423 P |
| 3,619,682 | 11/1971 | Newton et al. | 313/22 |
| 3,665,235 | 5/1972 | Hugot | 313/26 |
| 4,063,156 | 12/1977 | Patterson | 250/382 |
| 4,264,817 | 4/1981 | Newkermans et al. | 250/379 |
| 4,476,392 | 10/1984 | Young | 250/423 R |

FOREIGN PATENT DOCUMENTS 0094644 6/1982 Japan ................... 324/464

Primary Examiner—Bruce C. Anderson
Assistant Examiner—Paul A. Guss
Attorney, Agent, or Firm—Stevens, Davis, Miller & Mosher

[57] ABSTRACT

A thermal electron source suitable for use in an electron capture detector comprises a source of stable ultra-violet light, an ultra-violet transparent support member (20,31) located in the path of the ultra-violet light (41) and a thin photo-emissive metallic layer (1A, 24, 33) coated over the surface of the support member remote from the source. In one form the source is a cylindrical mercury vapor lamp (1) with the photo-emissive layer coated directly on the lamp. The coated lamp may then be enclosed within a cylindrical anode (8) with a gas flow between them and the electrical current is measured between the anode and cathode. In an alternative arrangement a planar geometrical assembly is provided. Preferably the photo-emissive material is gold and the carrier gas is an argon-methane mixture.

6 Claims, 3 Drawing Figures

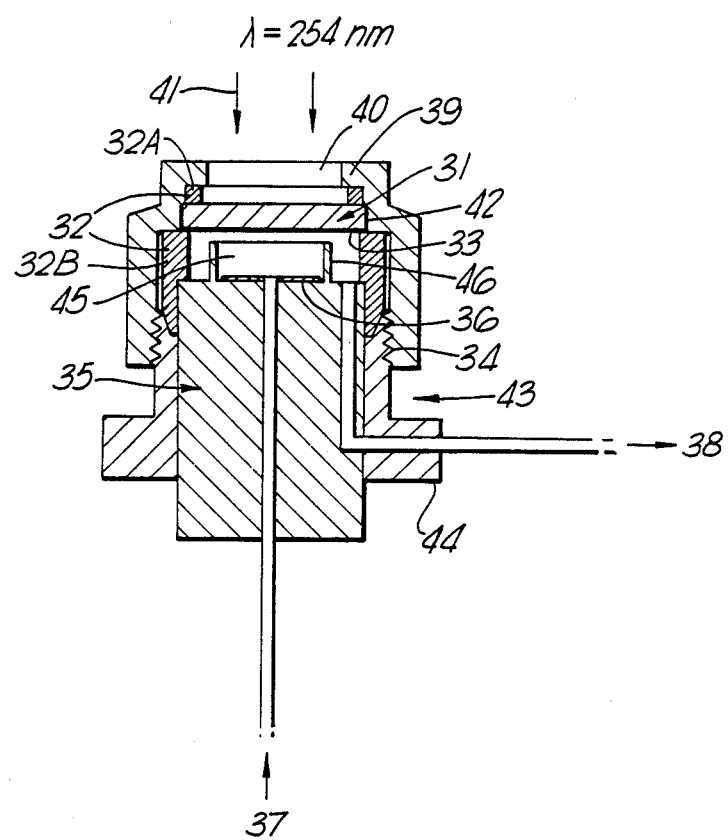

THERMAL ELECTRON SOURCE

The invention relates to sources of ionising radiation and more specifically to sources for producing low energy or thermal electrons.

Many ionisation detectors commonly used in analytical chemistry require radioactive sources to produce the primary ionization. For example, highly sensitive detectors for gas chromotography such as the electron capture detector (ECD) use a $\beta$ emitter normally $^3$H or $^{63}$Ni to produce thermal electrons by repeated collisions with molecules of a suitable carrier gas such as nitrogen or argon/methane. Other approaches to the production of near thermal electrons suitable for ionization detectors have included gaseous discharges, and thermionic emitters.

Non-radioactive ionization detectors are of considerable practical importance since they avoid the attendant health hazards of radioactive materials.

Conventional ECD's may require a long warm-up period from cold start of 12-24 hours before they are sufficiently stable for use. In addition, the chemistry involved in the use of known ECD's can be complicated by the production of positive ions in addition to negative charge carriers.

The object of the present invention is to produce a source of thermal electrons, overcoming some of the disadvantages experienced with conventional sources.

The invention provides a source of thermal electrons comprising:
 a source of stable ultra-violet light;
 an ultra-violet-transparent support member located in the path of the ultra violet light; and
 a thin photo-emissive metallic layer coated over at least a portion of the outer surface of the ultra-violet transparent support member;
 the metal being selected such that work function is less than the wavelength of principal irradiance of the light.

The term thin, used in relation to the metallic coating, is to be interpreted as a thickness selected as a compromise for optimum release of electrons and a fully conducting layer.

In one convenient arrangement the support member is the cylindrical envelope of an ultra-violet light source, the metallic coating being applied over at least a portion of the cylindrical surface.

In an alternative arrangement, providing cooling for the UV light source, the support member is in the form of a cylinder concentrically arranged around the UV light source such that a coolant may be passed through the annular space therebetween.

In a further arrangement the support member is planar thereby providing a source of thermal electrons suitable for linear geometrical applications in contrast to the cylindrical gometrical nature of the two foregoing arrangements.

Preferably the source of a low pressure memory lamp and the work function of metal is less than about 5 eV.

Advantageously the layer thickness is less than about 2000° A

In an arrangement suitable for use as an ECD, apparatus comprises: a cathode comprising a photo-emissive thermal electron source having a cylindrical geometry a larger diameter conducting cylindrical anode surrounding the cathode and extending along at least a portion of the length of the anode; and means to measure the current flow between the two electrodes. This current flow is assisted by the application of a DC potential difference between the anode and the cathode.

Advantageously there is provided means to vary the intensity of the ultra-violet light whereby the sensitivity of the photocathode of the ECD can be altered.

Advantageously the conducting cylinder is sealed at one end to a gas inlet capillary tube, the cylinder being supported by and insulated from one end of a metallic fitting, the other end of the fitting being electrically connected to the photo-emissive layer and having connected therethrough a gas outlet capillary tube. The cylinder is located within a close fitting glass cylinder, sealed at one end to the inlet gas capillary tube. In a particularly advantageous arrangement the ends of the metal fitting are provided with gas tight seals with respective threaded end caps to bear down on the seals. The seal to the photo-emissive surface is an electrically conducting graphitized ferrule.

The invention will now be described by reference to the examples illustrated in the accompanying drawings of which:

FIG. 3 shows a cross-section of an alternative end-window ECD.

Figure 1:
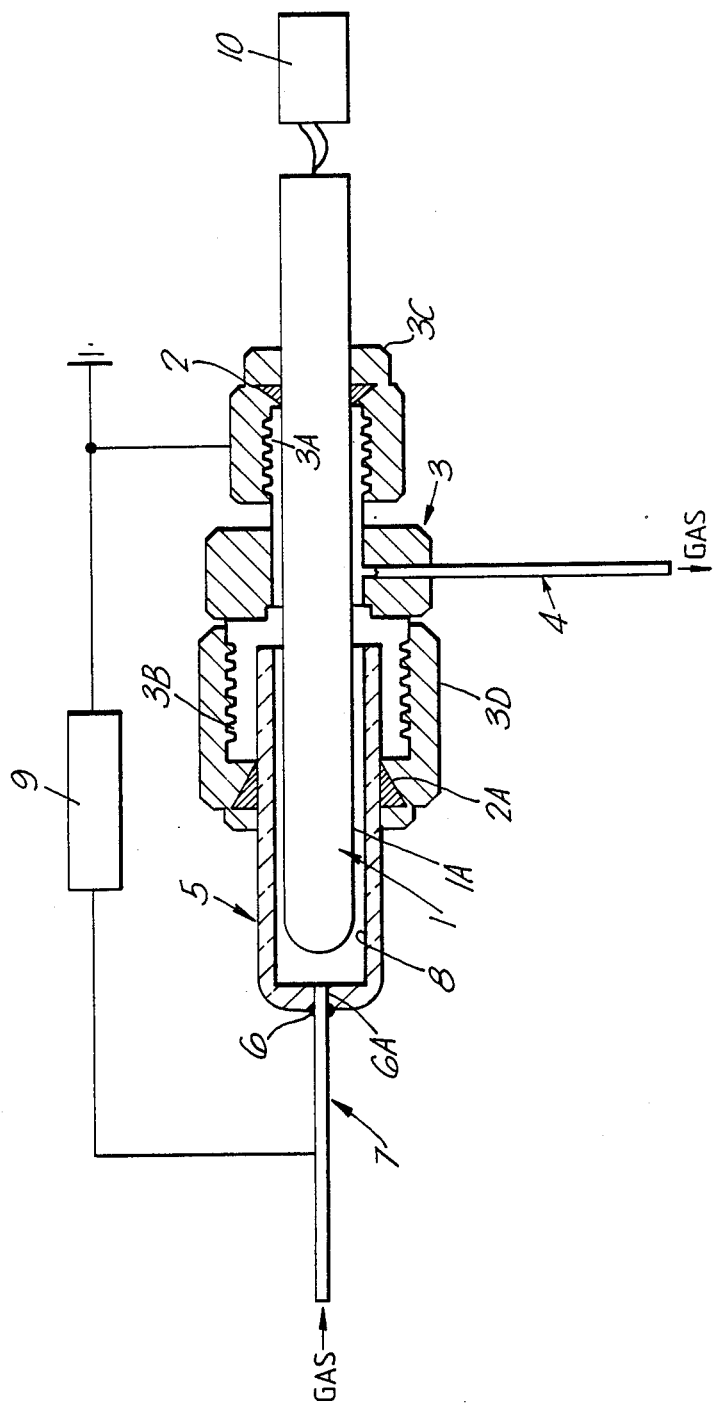
FIG. 1 is a cross-sectional view through an electron capture detector (ECD) incorporating the present thermal electron source.

The invention will now be described by way of example only with reference to the accompanying FIG. 1 illustrating a non-radioactive ECD.

A low pressure quartz mercury lamp (1) having a principal irradiance 254 nm, available from several commercial manufacturers, is coated with a very thin layer (1A) of metal eg gold or gold allows such as Pd/Au, Cs/Au and Cr/Au. All metals with work functions less than about 5 ev are potentially suitable, although for several practical reasons gold is often the preferred metal. The metal coating of the UV lamp can be most easily applied by vacuum sputtering or evaporation. A much thicker gold layer is deposited near the base of the lamp (approx 0.5 cm length) to make good electrical contact with a graphitised ferrule (2) which in turn locates the photocathode centrally within a stainless steel metal fitting (3) having externally threaded end portions (3A, 3B) engaged by respective threaded caps (3C, 3D). Attached to this fitting is a brazed 1/16 inch capillary tube (4) which serves as the gas exit port. The main body (5) of the detector can be fabricated from a variety of materials depending on the temperature requirements. Example of materials which can be used are metals, glass, ceramics or thermostable polymers such as Vespel (Trade Mark) or Teflon (Trade Mark). A further graphitized ferrule (2A) is provided to make a gas-tight seal between the main body (5) and the metal fitting (3). The end caps (3C) and (3D) bear respectively on the ferrules (2) and (2A) to seal the detector. A glass to metal seal (6), at the end of the detector body is fitted with a gas entry port (7) made of 1/16 inch capillary tubing. A stainless steel cylinder (8) is brazed (6A) to the capillary tube and fits tightly inside the inner glass wall of the main detector body. This structure together with the gas entry port also serves as the anode of the device and is connected to the measuring electrometer (9). The metal fitting (3) is grounded and together with the coated UV lamp forms the cathodic part of the electrical circuit. A purified carrier gas (low oxygen content <2 ppm) of Argon-Methane (95/5 by volume) or Nitrogen is introduced through the gas entry port (7) at a nominal flow rate of 50 ml/min, and exits the detector via the capillary tube (4). The preferred carrier gas, however, is Argon-Methane due to the very much high drift velocity of thermal electrons in this particular gass mixture. Overall sensitivity is lower in Nitrogen not only from the lower electron drift velocity but also due to appreciable backscattering of electrons to the source. Increasing the size and hence the surface area of the thermal electron source is largely effective in offsetting the inherent lower sensitivity in Nitrogen carrier gas, although there is a practical limit on size increase consistent with an acceptable detector mixing volume.

The thermal energy electron source thus described forms the basis of a non-radioactive ECD in which a characteristic decrease of background current measured by the electrometer (9) can be observed when chemical substances containing electrophoric groups enter the cell. Several modes of operation are possible, including constant voltage, constant current, and pulsed voltage. All of these will be familiar to those knowledgeable in the operation of the ECD.

The invention has been tested with a variety of packed and capillary chromatographic columns to compare its response with conventional radioactive electron capture detectors. The sensitivity has been found to be comparable to normal ECDs with a linear dynamic range of about three orders of magnitude. In addition to its principal advantage of being non-radioactive, the photocathode ECD appears to have a rapid warm-up from cold start, and is generally stable for use within 1-2 hours. Many commercially available ECD's require a warm-up period from cold of 12-14 hours before they are sufficiently stable for use. The sensitivity of the photocathode ECD can also be altered conveniently by providing means (10) to change the intensity of the UV radiation.

The theory of operation of the photocathode ECD is quite different from conventional radioactive ECD's since the photocathode produces only negative charge carriers, ie, electrons and some negative ions, principally $O_2^-$, since oxygen is difficult to totally exclude from the carrier gases used. Thus since no positive ions are produced the chemistry involved and hence the analytical understanding is considerably simplified.

For many applications in gas chromatography it is often desirable to operate the ionization detector at high temperatures (~350° C.) to ameliorate any effects of column bleed. The device described above is not designed for such high temperature operation, primarily due to a decrease in the UV light intensity from the lamp as the temperature is increased. The UV lamps currently available give their maximum UV output between 50°-85° C., and while the lamp has been operated successfully within a detector maintained at 200° C., sensitivity is considerably reduced as the light output shifts more into the visible range as the temperature increases. A second problem occurs a high temperatures caused by the tendency of thin metal films to form into "island" thus breaking electrical conduction through the photoemissive layer. To overcome this problem thermally stable metal layers must be deposited onto the quartz substrate using techniques of mixed metal and/or metal semiconductor layers, such as Cr/Au, and Sn/Au. These techniques are well known to those experienced in the deposition of thin metal films. To avoid direct heating of the UV lamp, the lamp can be easily positioned in the end-window arrangements, (FIG. 3) a short distance from the photoemissive window, and the UV light directed onto the window using fibre optices or focused with a lens of appropriate focal length. The method will again be familiar to those skilled in the art.

Figure 2:
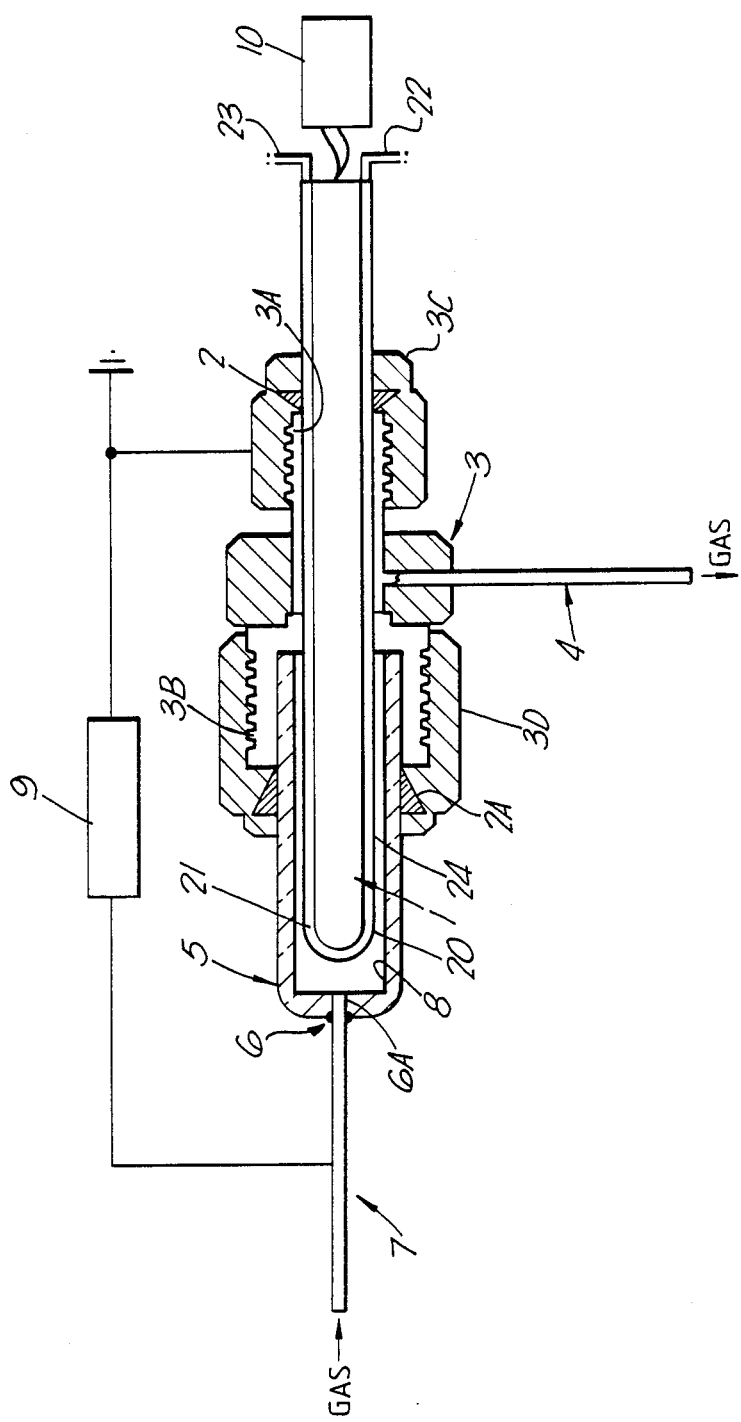
FIG. 2 is a modification of the ECD shown in FIG. 1, providing cooling for the source.

FIG. 2 shows a modification of the arrangement of FIG. 1 in which the light source is located in a cooled well. The low pressure mercury lamp 1 is supported with a Spectrasil (Trade Mark) high quality UV transparent cylindrical quartz tube 20 leaving an annular space 21 for circulation of a gaseous coolant via inlet and outlet pipes 22 and 23. The photo-emissive layer 24 is coated on a portion of the outside of the cylindrical tube 20 within the anode cylinder 8.

An alternative arrangement of ECD, detector departing from the cylindrical goemetries of FIGS. 1 and 2 is shown in FIG. 3. A "spectrosil" ultra-violet transmitting disc 31 is held by annular graphitised seals 32 within a threaded metallic nut 34. An inwardly projecting circular flange 39 provides a projection of the nut 34 against which one seal 32 is seated and the opening in the flange forms an end window 40 thorugh which UV light 41 can be directed. A thin gold cathode coating 33 is formed on the lower surface of the transparent disc 31. A thick gold annulus 42 surrounds the disc 31 and is in electrical contact with the coating 33. The graphitised seals 32 bear on the annulus 42 and complete an electrical connection from the metal nut 34 to the coating 33. The threaded portion of the nut 34 engages a complementary thread on the body 43 of the detector. The body 43 comprises an outer metallic annular portion 44 threaded at one end and which has supported therein a cylindrical insulator 35. A metal gas inlet pipe 37 passes through the body of the insulator 35 and makes contact with a circular anode 36 formed on the upper surface of the insulator 35. The lower seals 32B are formed with an inwardly directed annular flange forming respective seals for the transparent disc 31 and the insulator 35, thereby locating the anode 36 and cathode 33 in spaced parallel relationship. The gas inlet pipe 37 is thus connected to the inter-electrode space 45. A gas exit conduit 38 is also provided through the detector body 43 to the inter-electrode space 45. An annular baffle 46, integrally formed with the insulator 35 in the space 45 is provided between the axially positioned gas inlet and the circumferentially positioned gas outlet to provide a suitable path the for the gas flow between the anode and cathode of the detector.

A stable low power mercury vapour light source provides a constant source of UV light incident on the thin gold cathodic coating 33. As in the previous arrangements, the combination of suitably chosen UV light source and photo-cathode coating constitute a source of thermal electrons for the ECD detector. The cathode elctrode connection is taken from the metallic body of the detector and the anode connection is taken from the metal pipe 37.

Although the invention has been described with reference to its use in an ECD it should be apparent to those skilled in the art that the invention has much broader application. A thermal electron source of the type described above could also be a practical substitute for the radioactive source used in other ionization detectors, such as the electron mobility, and cross-section detectors. In addition to its potential use in these gas chromotography type detectors, a photoelectron source could also be used in a variety of other analytical applications. These include the use of a photo-cathode in the ion mobility detector (IMD) as a substitute for the conventional $^{63}$Ni radio-active source. In addition it can be used in mass spectrometers (MS) with specific application in the negative ion and chemical ionisation modes of operation. Additionally in MS which use an atmospheric ionisation source (APIS), also normally $^{63}$Ni, the thermal electron source is a practical substitute.

I claim:

1. An electron capture detector (ECD) including an anode and a cathode and means therebetween for passage of a gas stream including trace elements for detection wherein the cathode comprises:
    (a) a source of stable ultra-violet light having a cylindrical envelope;
    (b) a coating of photoemissive material provided over the cylindrical envelope of the source, the coating comprising a thin conducting layer of metal selected such that the work function is less than the principal irradiance of light, so that said source of stable ultra-violet light and said coating form a cathode having a photoemissive thermal electron source of cylindrical geometry; and
    (c) cathode connection means conductively connected to the photoemissive metallic layer such that electrical circuitry can be connected to the cathode.

2. An electron capture detector (ECD) including an anode and a cathode and means therebetween for passage of a gas stream including trace elements for detection wherein the cathode comprises:
    (a) a source of stable ultra-violet light having a cylindrical envelope;
    (b) a coating of photoemissive material provided over the cylindrical envelope of the source, the coating comprising a thin conducting layer of metal selected such that the work function is less than the principal irradiance of light, so that said source of stable ulta-violet light and said coating form a cathode having a photoemissive thermal electron source of cylindrical geometry;
    (c) cathode connection means conductively connected to the photoemissive metallic layer such that electrical circuitry can be connected to the cathode;
    (d) a conducting cylindrical anode having a larger diameter than and surrounding the cathode and extending along at least a portion of the length of the electron source,
    (e) means for introducing a flow of gas between the cathode and anode, and
    (f) means for measuring the current flow between the cathode and the anode.

3. An ECD as claimed in claim 2, further comprising a gas inlet capillary tube, a gas outlet capillary tube and a metallic fitting, and wherein the anode is sealed at one end to said gas inlet capillary tube, said anode is supported by and insulated from one end of said metallic fitting, the other end of the metallic fitting being electrically connected via the cathode connection means to said photoemissive metallic layer and having connected therethrough said gas outlet capillary tube.

4. An ECD as claimed in claim 3, further comprising a glass cylinder and wherein the anode is located within said glass cylinder, said glass cylinder closely fitting around said anode and being sealed at one end to the inlet gas capillary tube.

5. An ECD as claimed in claim 3 wherein the ends of the metallic fitting are provided with gas type seals between said metallic fitting and said photoemissive metallic layer and said conducting cylindrical anode and with respective threaded end caps to bear down on the seals.

6. An ECD as claimed in claim 5 wherein one of said gas tight seals which is located between said metallic fitting and the photoemissive metallic layer is an electrically conducting graphitized ferrule.

* * * * *